United States Patent
Wang et al.

(10) Patent No.: US 11,198,846 B2
(45) Date of Patent: Dec. 14, 2021

(54) MEDIUM FOR CULTURING BALANTIDIUM CTENOPHARYNGODONI IN VITRO, METHOD FOR PREPARING THE MEDIUM AND METHOD FOR CULTURING BALANTIDIUM CTENOPHARYNGODONI IN VITRO

(71) Applicant: Institute of Hydrobiology, Chinese Academy of Sciences, Hubei (CN)

(72) Inventors: Guitang Wang, Hubei (CN); Weishan Zhao, Hubei (CN); Ming Li, Hubei (CN); Shangong Wu, Hubei (CN); Hong Zou, Hubei (CN); Wenxiang Li, Hubei (CN); Fan Xiong, Hubei (CN)

(73) Assignee: Institute of Hydrobiology, Chinese Academy of Sciences, Hubei (CN)

( * ) Notice: Subject to any disclaimer, the term of this patent is extended or adjusted under 35 U.S.C. 154(b) by 279 days.

(21) Appl. No.: 16/611,844

(22) PCT Filed: May 11, 2018

(86) PCT No.: PCT/CN2018/086471
§ 371 (c)(1),
(2) Date: Nov. 7, 2019

(87) PCT Pub. No.: WO2019/200637
PCT Pub. Date: Oct. 24, 2019

(65) Prior Publication Data
US 2021/0144977 A1 May 20, 2021

(30) Foreign Application Priority Data
Apr. 18, 2018 (CN) .......................... 201810350529.4

(51) Int. Cl.
A01K 67/033 (2006.01)
C12N 1/00 (2006.01)
C12N 1/10 (2006.01)
C12N 5/00 (2006.01)

(52) U.S. Cl.
CPC ................. *C12N 1/00* (2013.01); *C12N 1/10* (2013.01); *C12N 5/0068* (2013.01)

(58) Field of Classification Search
CPC ................................ A01K 67/033; C12N 5/00
See application file for complete search history.

(56) References Cited

FOREIGN PATENT DOCUMENTS

| CN | 1251529 A | 4/2000 |
|----|-----------|--------|
| CN | 104293672 | 1/2015 |
| SU | 1406154 | 10/1981 |

OTHER PUBLICATIONS

Wang T. et al. (CN104293672A—USPTO—Machine Translation—ENGLISH)—"In-vitro culture method of *Balantidium coli*" (total 17 pages-of English translation). (Year: 2015).*
Zhao W. et al., "Identification of Intracellular Bacteria in the Ciliate *Balantidium ctenopharyngodoni* (Ciliophora, Litostomatea)", Journal of Eukaryotic Microbiology 2020, vol. 67, pp. 417-426. (Year: 2020).*
Clark C.G. et al., "Methods for Cultivation of Luminal Parasitic Protists of Clinical Importance", Clinical Microbiology Reviews, Jul. 2002, vol. 15, No. 3, pp. 329-341. (Year: 2002).*
Kalman Molnar and Mikios Reinhardt, 2. Intestinal lesions in grasscarp *Ctenopharyngodon idella* (Valenciennes) infected with Balantidium ctenopharyngodonis Chen, Journal of Fish Diseases, 1978, 1, 151-156,.
Light and scanning electron microscopic study of Balantidium ctenopharyngodoni Chen, 1955 (Class: Litostomatea) from China, Ming Li and etal, Parasitol Res (2007) 101:185-192.
New insights into the molecular phylogeny of Balantidium 9Ciliophora, Vetibuliferida) based on the analysis of new sequences of spcies from fish hosts, Ming Li et al., Parasitol Res 113 : 4327-4333 (2014).
Molecular genetic investigations on Balantidium ctenopharyngodoni Chen, 1955, a parasite of the grass carp (*Ctenopharyngodon idella*), Szilvia Marton and et al, Acta Veterinaria Hungarica 64(2), pp. 213-221 (2016) DOI: 10.1556/004.20163021.

\* cited by examiner

*Primary Examiner* — Satyendra K Singh

(57) ABSTRACT

A medium for culturing *Balantidium ctenopharyngodoni* in vitro, method for preparing the medium and method for culture in vitro are provided, which belongs to technical field of in vitro culture of intestinal protozoa. The formulation of the culture medium includes: 100 ml of Ringer's solution, 0.5 g of yeast extract, 1.0 g of proteose peptone, 3-6 ml of fetal bovine serum, 6-10 ml of horse serum, 300-500 µl of *Bacillus licheniformis* suspension, 200-300 mg of aseptic starch. Culture steps include: inoculating collected *Balantidium ctenopharyngodoni* into a prepared medium, filling with nitrogen and sealing, culturing at 15° C. for 48-72 hours, then transferring to another fresh medium, cycling back and forth, proliferating the *Balantidium ctenopharyngodoni* continuously. *Balantidium ctenopharyngodoni* are capable of achieving cell division and proliferation in the culture medium, and lays foundation for the physiological and experimental ecology research of the *Balantidium ctenopharyngodoni*.

10 Claims, 1 Drawing Sheet

MEDIUM FOR CULTURING BALANTIDIUM CTENOPHARYNGODONI IN VITRO, METHOD FOR PREPARING THE MEDIUM AND METHOD FOR CULTURING BALANTIDIUM CTENOPHARYNGODONI IN VITRO

CROSS REFERENCE OF RELATED APPLICATION

This is a U.S. National Stage under 35 U.S.C 371 of the International Application PCT/CN2018/086471, filed May 11, 2018, which claims priority under 35 U.S.C. 119(a-d) to CN 201810350529.4, filed Apr. 18, 2018.

BACKGROUND OF THE PRESENT INVENTION

Field of Invention

The present invention relates to the technical field of in vitro culture of parasitic protozoa, and more particularly to a medium for culturing Balantidium ctenopharyngodoni in vitro, a method for preparing the medium and a method for culturing the Balantidium ctenopharyngodoni in vitro.

Description of Related Arts

Balantidium ctenopharyngodoni is an obligatory intestinal ciliate of the grass carp that was first discovered and named by Prof. Chen Qiliu (1955). Molnár and Reinhardt (1978) found that it mainly inhabits the mucosal folds and luminal contents of the hindgut using histological examination methods, and the proliferation of the ciliates may cause the enteritis in the hindgut, and may cause inflammation of other intestinal segments of the grass carp. Li Ming et al. (2007, 2014) observed the ciliates by hematoxylin staining, scanning electron microscopy and then described the morphological characteristics of the ciliates systematically and comprehensively, and studied the phylogenetic position of the Balantidium ctenopharyngodoni and the relationships among Balantidium members and other related Vestibuliferida species using 18S rRNA sequences.

Except Balantioides coli—an important and mostly researched pathogen in the digestive tract of mammalian, little is known about the pathology of other species of the family Balantidiidae. It is the same case for the Balantidium ctenopharyngodoni—the relationship between this ciliate and its host grass carp (parasitic or symbiotic) is still unknown. Although the cyst form of the Balantidium ctenopharyngodoni was found during the former studies, it is still unclear whether the cyst form is the infective stage of the balantidium. And because its host grass carp lives in a complex water environment, people are ignorant of the information on the path of infection. Some researchers have found that when grass carp suffer from intestinal hemorrhagic disease, the number of the Balantidium ctenopharyngodoni was significantly increased, so this ciliate was inferred to be harmful to grass carp. However, some others thought that the Balantidium ctenopharyngodoni had a certain symbiotic relationship with grass carp because there was no Balantidium ctenopharyngodoni infection in the juvenile fish of grass carp. Infections can be found when the hosts change their feeding habits to herbivory. This fact naturally reminds us that the Balantidium ctenopharyngodoni may be closely related to the digestion and utilization of cellulose just like the rumen ciliates.

In order to further explore the infection form of the Balantidium ctenopharyngodoni, and carry out biological research on its life history, pathogenesis and relationship to its host, it is essential to establish a stable and efficient in-vitro culture system of the Balantidium ctenopharyngodoni. Before the present invention was made, reports all over the world on the Balantidium ctenopharyngodoni were mainly focused on morphological and epidemiological studies. At present, there was no research report on the medium composition and culture method for in vitro culture of the Balantidium ctenopharyngodoni.

SUMMARY OF THE PRESENT INVENTION

An object of the present invention is to overcome the deficiencies of the conventional art, and to provide a medium for culturing Balantidium ctenopharyngodoni in vitro, a method for preparing the medium and a method for culturing the Balantidium ctenopharyngodoni in vitro.

Accordingly, in order to achieve the first object mentioned above, a technical solution adopted by the present invention is as follows.

A medium for culturing the Balantidium ctenopharyngodoni in vitro is provide by the preset invention, comprising: 100 ml of Ringer's solution, 0.5 g of yeast extract, 1.0 g of proteose peptone, 3-6 ml of fetal bovine serum, 6-10 ml of horse serum, 300-500 µl of Bacillus licheniformis suspension, 200-300 mg of aseptic starch.

Preferably, formulation ingredients and content of the Ringer's solution comprise: 6.5 g of sodium chloride (NaCl), 0.14 g of potassium chloride (KCl), 0.12 g of calcium chloride ($CaCl_2$), 0.2 g of sodium bicarbonate ($NaHCO_3$), 0.01 g of sodium dihydrogen phosphate ($NaH_2PO_4$) and 1000 ml of distilled water.

A second object of the present invention is to provide a method for preparing the medium for culturing the Balantidium ctenopharyngodoni in vitro specifically comprising steps of:

(a) accurately weighing 0.5 g of yeast extract and 1.0 g of proteose peptone, adding 100 ml of Ringer's solution, adjusting a pH to 7.0-7.5, autoclaving and then storing at 4° C.;

(b) split charging a plurality of sterile anaerobic bottles with a medium formed in the step (a) by a volume of 3-5 ml, and separately adding 9-25 µl of Bacillus licheniformis suspension to each of the sterile anaerobic bottles, and sending the plurality of the sterile anaerobic bottles into a microbial shaker at 30° C. for culturing until a concentration is $2 \times 10^9$-$6 \times 10^9$ CFU/ml;

(c) respectively adding 90-250 µl of fetal bovine serum, 180-500 µl of horse serum and 6-15 mg of aseptic starch to each of the sterile anaerobic bottles containing the medium formed in the step (b), and then placing at 15° C. for use.

Preferably, an autoclaving temperature in the step (a) is 121° C., and an autoclaving time is 20 min.

Preferably, a speed of the microbial shaker in the step (b) is 150 rpm

Preferably, the Ringer's solution is prepared by steps of:

(i) sequentially dissolving 6.5 g of sodium chloride, 0.14 g of potassium chloride, 0.2 g of sodium bicarbonate, and 0.01 g of sodium dihydrogen phosphate in 999 ml distilled water to prepare a solution 1;

(ii) preparing a $CaCl_2$ solution having a mass concentration of 12%; and (iii) adding 1 ml of the $CaCl_2$ solution in the step (ii) to the solution 1, and mixing uniformly to obtain the Ringer's solution, storing at room temperature for use.

A third object of the present invention is to provide a method for culturing the *Balantidium ctenopharyngodoni* in vitro, comprising steps of:

(1) preparing a plurality of anaerobic bottles sterilized, wherein each of the anaerobic bottles contain 3-5 ml of the medium mentioned above cultured in vitro;

(2) dissecting an intestine of a grass carp, collecting the *Balantidium ctenopharyngodoni* under an stereomicroscope, placing the *Balantidium ctenopharyngodoni* in a sterile petri dish containing aseptic saline solution, gently washing 2 to 3 times, replacing the aseptic saline, then placing in a constant temperature incubator at 15° C. and standing for a period of time;

(3) taking out free ciliates in the petri dish after standing in the step (2) under the stereomicroscope, inoculating into one of the anaerobic bottles in the step (1), continuously filling nitrogen for 3-5 minutes, and then sealing the bottle with rubber stopper, putting the anaerobic bottles at a constant temperature of 15° C. for culturing 48-72 h;

(4) transferring all the ciliates in the anaerobic bottles to a next anaerobic bottle after a previous step (3) of constant temperature culture, then fill the anaerobic bottle with nitrogen for 3-5 minutes, then sealing, and culturing at identical conditions follows previous step (3), repeating transferring and culturing every 48-72 hours to proliferate the *Balantidium ctenopharyngodoni* continuously.

Preferably, in the method for culturing the *Balantidium ctenopharyngodoni* in vitro, the aseptic saline solution has a mass volume concentration of 0.65%.

Preferably, the nitrogen is pure nitrogen and a purity of nitrogen is greater than 99.99%.

Preferably, the standing time of the step (2) is at a range of 20-30 minutes.

Preferably, in the above technical solution step (2), the collection of the *Balantidium ctenopharyngodoni*, the removal and transfer of the *Balantidium ctenopharyngodoni* are all sucked by an aseptic glass micropipettes in the steps (3) and (4).

The medium for culturing the *Balantidium ctenopharyngodoni* in vitro of the preset invention is prepared by on a basis of yeast extract and proteose peptone, and then adding inorganic salts, *Bacillus licheniformis* suspension, fetal bovine serum, horse serum and aseptic starch.

Compared with the conventional art, the present invention has beneficial effects as follows.

(1) The preparation method of the medium of the present invention is simple, and it is not necessary to add other complicated components.

(2) The culture method of the invention is simple, and the apparatus and equipment adopted are few, and can be cultured under ordinary laboratory conditions.

(3) The *Balantidium ctenopharyngodoni* is cultured in the medium prepared by the present invention, and the division and proliferation can be achieved, and after continuous culture for one year, the *Balantidium ctenopharyngodoni* still maintains vigorous vitality and fecundity.

DETAILED DESCRIPTION OF THE PREFERRED EMBODIMENT

Figure 1:
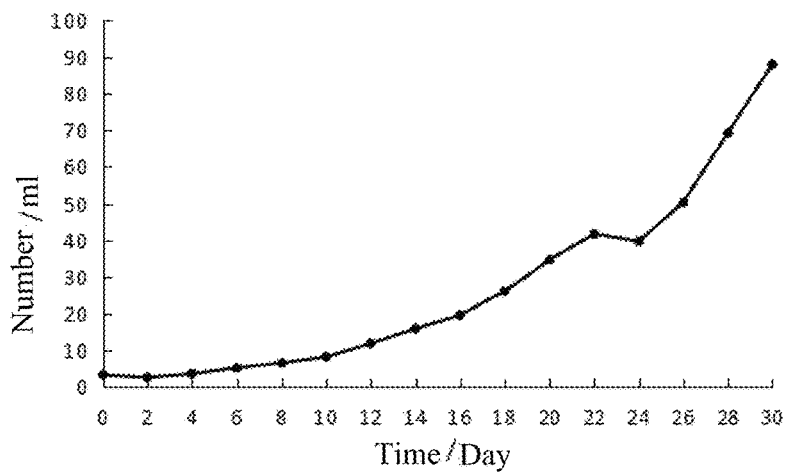
FIG. 1 is a growth curve diagram of *Balantidium ctenopharyngodoni* cultured in a medium in vitro according to an Example 1 of the present invention.

The precise description of the present invention may be susceptible to various modifications of the present invention without departing from the spirit and scope of the appended claims. It is to be understood that the scope of the invention is not to be construed. In fact, it is apparent to those skilled in the art that the various modifications of the embodiments of the invention are possible within the scope of the appended claims.

In order to better understand the invention and not to limit the scope of the invention, all numbers and percentages used in the present application, as well as other values, are to be understood in all instances as modified by the word "about". Accordingly, unless otherwise stated, the numerical parameters set forth in the specification and the appended claims are an approximation, which may vary depending on the desired properties sought to be obtained. The individual numerical parameters should at least be considered as being based on the reported significant figures and by conventional rounding methods.

In the following examples, the *Balantidium ctenopharyngodoni* were collected from the grass carp in the Liangzi Lake of Wuhan City, Hubei Province, China, and the grass carp was brought back to the laboratory for anatomy, and isolation of ciliates.

Example 1

According to an Example 1 of the present invention, a medium for culturing *Balantidium ctenopharyngodoni* in vitro is provide by the preset invention, comprising: 100 ml of Ringer's solution, 0.5 g of yeast extract, 1.0 g of proteose peptone, 3.5 ml of fetal bovine serum, 10 ml of horse serum, 335 μl of *Bacillus licheniformis* suspension, 300 mg of aseptic starch.

Preferably, formulation ingredients and content of the Ringer's solution comprise: 6.5 g of sodium chloride (NaCl), 0.14 g of potassium chloride (KCl), 0.12 g of calcium chloride ($CaCl_2$), 0.2 g of sodium bicarbonate ($NaHCO_3$), 0.01 g of sodium dihydrogen phosphate ($NaH_2PO_4$) and 1000 ml of distilled water.

The Ringer's solution is prepared by the method as follows, which comprises steps of:

(i) sequentially dissolving 6.5 g of sodium chloride, 0.14 g of potassium chloride, 0.2 g of sodium bicarbonate, and 0.01 g of sodium dihydrogen phosphate in 999 ml distilled water to prepare a solution 1;

(ii) preparing a $CaCl_2$ solution having a mass concentration of 12%; and (iii) adding 1 ml of the $CaCl_2$ solution in the step (ii) to the solution 1, and mixing uniformly to obtain the Ringer's solution, storing at room temperature for use.

In the Example 1 of the present invention, a method for preparing the medium for culturing the *Balantidium ctenopharyngodoni* in vitro, specifically comprising steps of:

(a) accurately weighing 0.5 g of yeast extract and 1.0 g of proteose peptone, to be put into a conical flask with a volume of 250 ml, adding 100 ml of Ringer's solution, adjusting a pH to 7.0-7.5, sealing the conical flask with foil paper, autoclaving at 121° C. for 20 min and then storing after the medium is cooled to 4° C.;

(b) split charging each of a plurality of 25 ml sterile anaerobic bottles with a 3 ml medium formed in the step (a), and separately adding 10 μl of *Bacillus licheniformis* suspension to each of the sterile anaerobic bottles, and putting the plurality of the sterile anaerobic bottles into a microbial shaker at 30° C. for culturing until a concentration is $3 \times 10^9$ CFU/ml, wherein a rotation speed of the shaker is 150 rpm;

(c) respectively adding 100 μl of fetal bovine serum, 300 μl of horse serum and 9 mg of aseptic starch to each of the sterile anaerobic bottles containing the medium formed in the step (b), and then placing at 15° C. for use, wherein at this time, the medium for culturing the *Balantidium ctenopharyngodoni* in vitro is completed.

A method for culturing the *Balantidium ctenopharyngodoni* in vitro, comprising steps of:

(1) taking out a plurality of anaerobic bottles containing the medium for culturing the *Balantidium ctenopharyngodoni* cultured in vitro;

(2) anesthetizing the grass carp with MS-222 to be put into a dissection tray, rinsing a anus near with sterile water, dissecting the grass carp with a sterile anatomical scissors, taking out viscera, cutting the hindgut to be put into a sterile petri dish with a diameter of 9 cm; opening the hindgut with a small anatomical scissors, and scraping luminal contents of the hindgut with a sterile scalpel to be put into a sterile petri dish with a diameter of 5.5 cm; adding 5 ml of sterile saline solution with a concentration of 0.65% (w/v); standing for 3 min; examining the *Balantidium ctenopharyngodoni* inhabited in the contents of the hindgut under a stereomicroscope; after finding the *Balantidium ctenopharyngodoni*, aspirating them with a sterile glass micropipette to another petri dish containing sterile saline with a concentration of 0.65% (w/v); after washing 3 times, replacing with new sterile saline, and placing in a constant temperature incubator at 15° C. for 25 min;

(3) taking out the medium in the constant temperature incubator and the petri dish containing the *Balantidium ctenopharyngodoni*, and taking 10 active *Balantidium ctenopharyngodoni* with a sterile glass micropipette to be inoculated to a anaerobic bottle containing the medium for the *Balantidium ctenopharyngodoni*, sealing the anaerobic bottle with rubber stopper after being continuously filled with nitrogen for 3 minutes, and placing in a constant temperature incubator at 15° C. for 48 hours;

(4) taking out the anaerobic bottle containing ciliates in the constant temperature incubator, pouring out the culture into a sterile petri dish, and transferring all the *Balantidium ctenopharyngodoni* to another anaerobic bottle containing 3 ml of fresh medium for culturing the *Balantidium ctenopharyngodoni* in vitro with a sterile glass micropipette under a stereomicroscope, and meanwhile recording a number of the *Balantidium ctenopharyngodoni*, then filling the anaerobic bottle with nitrogen for 3 min and sealing, then continuing to place in constant temperature incubator at 15° C. for 48 hours;

(5) transferring all the *Balantidium ctenopharyngodoni* after the constant temperature culture in step (4) in the anaerobic bottle to another anaerobic bottle, and meanwhile recording a number of all the *Balantidium ctenopharyngodoni*, then filling the anaerobic bottle with nitrogen for 3 min and sealing, then continuing to place in constant temperature incubator at a 15° C. for 48 hours; (6) transferring all the *Balantidium ctenopharyngodoni* after the constant temperature culture in step (5) in the anaerobic bottle to another anaerobic bottle, repeating transferring and culturing once every 48 hours to make the *Balantidium ctenopharyngodoni* continuing to multiply, and preparing fresh medium for culturing the *Balantidium ctenopharyngodoni* in vitro in time during the experiment.

The nitrogen mentioned above is pure nitrogen and a purity of nitrogen is greater than 99.99%.

In the Example 1, the in vitro culture experiment of the *Balantidium ctenopharyngodoni* continued for one year, and the *Balantidium ctenopharyngodoni* were observed and counted once every 48 hours. Take a number of the *Balantidium ctenopharyngodoni* in the first month and generate growth curve, which is as shown in FIG. 1. It can be seen from FIG. 1 that during this one-month period, the *Balantidium ctenopharyngodoni* in the medium remained strong fertility and vitality, and the growth curve tends to grow continuously.

Figure 2:
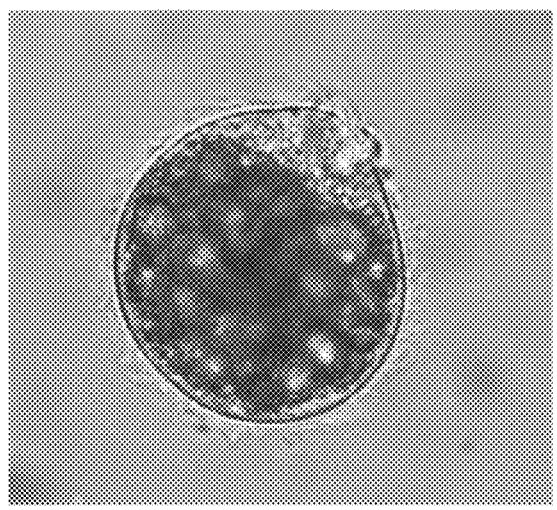
FIG. 2 is a diagram showing a living *Balantidium ctenopharyngodoni* observed under a microscope after being cultured for 30 days in vitro in the Example 1 of the present invention.
Figure 3:
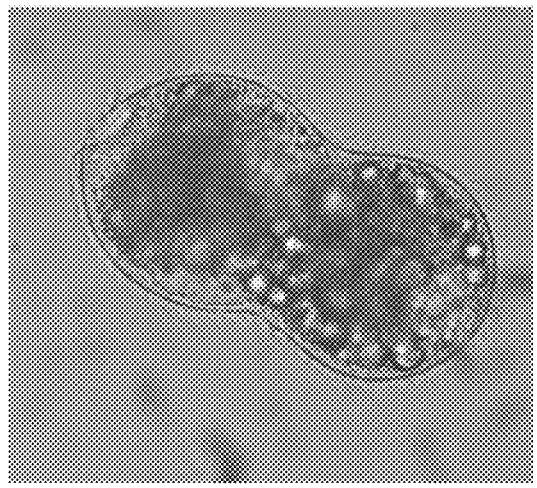
FIG. 3 is a view showing cell division of the *Balantidium ctenopharyngodoni* which are observed under the microscope after being cultured for 30 days in vitro in the Example 1 of the present invention.

FIG. 2 and FIG. 3 are respectively two figures showing a living *Balantidium ctenopharyngodoni* and division of the *Balantidium ctenopharyngodoni* which are observed under a stereomicroscope after being cultured for 30 days in vitro in the Example 1 of the present invention. As can be seen from FIG. 2 and FIG. 3, the present invention enables the cell division and long-term stable culture of the *Balantidium ctenopharyngodoni* in the medium cultured in vitro, and maintains vigorous vitality and fecundity during the cultivation process. The present invention has laid a solid foundation for the physiology and experimental ecology of the *Balantidium ctenopharyngodoni*.

Example 2

According to the Example 2 of the present invention, a medium for culturing *Balantidium ctenopharyngodoni* in vitro is provide by the preset invention, comprising: 100 ml of Ringer's solution, 0.5 g of yeast extract, 1.0 g of proteose peptone, 3 ml of fetal bovine serum, 6 ml of horse serum, 300 μl of *Bacillus licheniformis* suspension, 200 mg of aseptic starch.

In the Example 2, formulas and preparing method of the Ringer's solution are identical to the Example 1.

In the Example 2 of the present invention, a method for preparing the medium for culturing the *Balantidium ctenopharyngodoni* in vitro, specifically comprising steps of:

(a) accurately weighing 0.5 g of yeast extract and 1.0 g of proteose peptone, to be put into a conical flask with a volume of 250 ml, adding 100 ml of Ringer's solution, adjusting a pH to 7.0-7.5, sealing the conical flask with foil paper, autoclaving at 121° C. for 20 min and then storing after the medium is cooled to 4° C.;

(b) split charging each of a plurality of 25 ml sterile anaerobic bottles with a 3 ml medium formed in the step (a), and separately adding 9 μl of *Bacillus licheniformis* suspension to each of the sterile anaerobic bottles, and putting the plurality of the sterile anaerobic bottles into a microbial shaker at 30° C. for culturing until a concentration is $6 \times 10^9$ CFU/ml, wherein a rotation speed of the shaker is 150 rpm;

(c) respectively adding 90 μl of fetal bovine serum, 180 μl of horse serum and 6 mg of aseptic starch to each of the sterile anaerobic bottles containing the medium formed in the step (b), and then placing at 15° C. for use, wherein at this time, the medium for culturing the *Balantidium ctenopharyngodoni* in vitro is completed.

A method for culturing the *Balantidium ctenopharyngodoni* in vitro, comprising steps of:

(1) taking out a plurality of anaerobic bottles containing the medium for culturing the *Balantidium ctenopharyngodoni* cultured in vitro;

(2) anesthetizing the grass carp with MS-222 to be put into a dissection tray, rinsing a anus near with sterile water, dissecting the grass carp with a sterile anatomical scissors, taking out viscera, cutting the hindgut to be put into a sterile petri dish with a diameter of 9 cm; opening the hindgut with a small anatomical scissors, and scraping luminal contents of the hindgut with a sterile scalpel to be put into a sterile petri dish with a diameter of 5.5 cm; adding 5 ml of sterile saline solution with a concentration of 0.65% (w/v); standing for 3 min; examining the *Balantidium ctenopharyngodoni* inhabited in the contents of the hindgut under a stereomicroscope; after finding the *Balantidium ctenopharyngodoni*, aspirating them with a sterile glass micropipette to another petri dish containing sterile saline with a concentration of 0.65% (w/v); after washing 3 times, replacing with new sterile saline, and placing in a constant temperature incubator at 15° C. for 20 min;

(3) taking out the medium in the constant temperature incubator and the petri dish containing the *Balantidium ctenopharyngodoni*, and taking 10 active *Balantidium ctenopharyngodoni* with a sterile glass micropipette to be inoculated to a anaerobic bottle containing the medium for the *Balantidium ctenopharyngodoni*, sealing the anaerobic bottle with rubber stopper after being continuously filled with nitrogen for 5 minutes, and placing in a constant temperature incubator at 15° C. for 72 hours;

(4) taking out the anaerobic bottle containing ciliates in the constant temperature incubator, pouring out the culture into a sterile petri dish, and transferring all the *Balantidium ctenopharyngodoni* to another anaerobic bottle containing 3 ml of fresh medium for culturing the *Balantidium ctenopharyngodoni* in vitro with a sterile glass micropipette under a stereomicroscope, and meanwhile recording a number of the *Balantidium ctenopharyngodoni*, then filling the anaerobic bottle with nitrogen for 5 min and sealing, then continuing to place in constant temperature incubator at a 15° C. for 72 hours;

(5) transferring all the *Balantidium ctenopharyngodoni* after the constant temperature culture in step (4) in the anaerobic bottle to another anaerobic bottle, and meanwhile recording a number of all the *Balantidium ctenopharyngodoni*, then filling the anaerobic bottle with nitrogen for 5 min and sealing, then continuing to place in constant temperature incubator at a 15° C. for 72 hours; (6) transferring all the *Balantidium ctenopharyngodoni* after the constant temperature culture in step (5) in the anaerobic bottle to another anaerobic bottle, repeating transferring and culturing once every 72 hours to make the *Balantidium ctenopharyngodoni* continuing to multiply, and preparing fresh medium for culturing the *Balantidium ctenopharyngodoni* in vitro in time during the experiment.

The nitrogen mentioned above is pure nitrogen and a purity of nitrogen is greater than 99.99%.

In the Example 2, the in vitro culture experiment of the *Balantidium ctenopharyngodoni* continued for one year, and the *Balantidium ctenopharyngodoni* were observed and counted once every 72 hours. During this one-year period, the *Balantidium ctenopharyngodoni* in the medium remained strong fertility and vitality.

In addition, the applicants respectively observed a living *Balantidium ctenopharyngodoni* and cell division of the *Balantidium ctenopharyngodoni* under a microscope after being cultured for 1 year in vitro. The result indicates that the medium prepared by the present invention enables the cell division and long-term stable culture of the *Balantidium ctenopharyngodoni*, and maintains vigorous vitality and fecundity during the cultivation process.

Example 3

According to the Example 3 of the present invention, a medium for culturing *Balantidium ctenopharyngodoni* in vitro is provide by the preset invention, comprising: 100 ml of Ringer's solution, 0.5 g of yeast extract, 1.0 g of proteose peptone, 6 ml of fetal bovine serum, 9 ml of horse serum, 335 µl of *Bacillus licheniformis* suspension, 250 mg of aseptic starch.

In the Example 3, formulas and preparing method of the Ringer's solution are identical to the Example 1.

In the Example 3 of the present invention, a method for preparing the medium for culturing the *Balantidium ctenopharyngodoni* in vitro, specifically comprising steps of:

(a) accurately weighing 0.5 g of yeast extract and 1.0 g of proteose peptone, to be put into a conical flask with a volume of 250 ml, adding 100 ml of Ringer's solution, adjusting a pH to 7.0-7.5, sealing the conical flask with foil paper, autoclaving at 121° C. for 20 min and then storing after the medium is cooled to 4° C.;

(b) split charging each of a plurality of 25 ml sterile anaerobic bottles with a 3 ml medium formed in the step (a), and separately adding 10 µl of *Bacillus licheniformis* suspension to each of the sterile anaerobic bottles, and putting the plurality of the sterile anaerobic bottles into a microbial shaker at 30° C. for culturing until a concentration is $2\times10^9$ CFU/ml, wherein a rotation speed of the shaker is 150 rpm;

(c) respectively adding 180 µl of fetal bovine serum, 270 µl of horse serum and 7.5 mg of aseptic starch to each of the sterile anaerobic bottles containing the medium formed in the step (b), and then placing at 15° C. for use, wherein at this time, the medium for culturing the *Balantidium ctenopharyngodoni* in vitro is completed.

A method for culturing the *Balantidium ctenopharyngodoni* in vitro, comprising steps of:

(1) taking out a plurality of anaerobic bottles containing the medium for culturing the *Balantidium ctenopharyngodoni* cultured in vitro;

(2) anesthetizing the grass carp with MS-222 to be put into a dissection tray, rinsing a anus near with sterile water, dissecting the grass carp with a sterile anatomical scissors, taking out viscera, cutting the hindgut to be put into a sterile petri dish with a diameter of 9 cm; opening the hindgut with a small anatomical scissors, and scraping luminal contents of the hindgut with a sterile scalpel to be put into a sterile petri dish with a diameter of 5.5 cm; adding 5 ml of sterile saline solution with a concentration of 0.65% (w/v); standing for 3 min; examining the *Balantidium ctenopharyngodoni* inhabited in the contents of the hindgut under a stereomicroscope; after finding the *Balantidium ctenopharyngodoni*, aspirating them with a sterile glass micropipette to another petri dish containing sterile saline with a concentration of 0.65% (w/v); after washing 3 times, replacing with new sterile saline, and placing in a constant temperature incubator at 15° C. for 30 min;

(3) taking out the medium in the constant temperature incubator and the petri dish containing the *Balantidium ctenopharyngodoni*, and taking 10 active *Balantidium ctenopharyngodoni* with a sterile glass micropipette to be inoculated to a anaerobic bottle containing the medium for the *Balantidium ctenopharyngodoni*, sealing the anaerobic bottle with rubber stopper after being continuously filled with nitrogen for 4 minutes, and placing in a constant temperature incubator at 15° C. for 60 hours;

(4) taking out the anaerobic bottle containing ciliates in the constant temperature incubator, pouring out the culture into a sterile petri dish, and transferring all the *Balantidium ctenopharyngodoni* to another anaerobic bottle containing 3 ml of fresh medium for culturing the *Balantidium ctenopharyngodoni* in vitro with a sterile glass micropipette under a stereomicroscope, and meanwhile recording a number of the *Balantidium ctenopharyngodoni*, then filling the anaerobic bottle with nitrogen for 4 min and sealing, then continuing to place in constant temperature incubator at 15° C. for 60 hours;

(5) transferring all the *Balantidium ctenopharyngodoni* after the constant temperature culture in step (4) in the anaerobic bottle to another anaerobic bottle, and meanwhile recording a number of all the *Balantidium ctenopharyngodoni*, then filling the anaerobic bottle with nitrogen for 4 min and sealing, then continuing to place in constant temperature incubator at a 15° C. for 60 hours;

(6) transferring all the *Balantidium ctenopharyngodoni* after the constant temperature culture in step (5) in the anaerobic bottle to another anaerobic bottle, repeating transferring and culturing once every 60 hours to make the *Balantidium ctenopharyngodoni* continued to multiply, and preparing fresh medium for culturing the *Balantidium ctenopharyngodoni* in vitro in time during the experiment.

The nitrogen mentioned above is pure nitrogen and a purity of nitrogen is greater than 99.99%.

In the Example 3, the in vitro culture experiment of the *Balantidium ctenopharyngodoni* continued for one year, and the *Balantidium ctenopharyngodoni* were observed and counted once every 60 hours. During this one-year period, the *Balantidium ctenopharyngodoni* in the medium remained strong fertility and vitality.

In addition, the applicants respectively observed a living *Balantidium ctenopharyngodoni* and cell division of the *Balantidium ctenopharyngodoni* under a microscope after being cultured for 1 year in vitro of the present invention. The result indicates that the medium prepared by the present invention enables the split-proliferation cell division and long-term stable culture of the *Balantidium ctenopharyngodoni*, and maintains vigorous vitality and fecundity during the cultivation process.

Example 4

According to the Example 4 of the present invention, a medium for culturing *Balantidium ctenopharyngodoni* in vitro is provide by the preset invention, comprising: 100 ml of Ringer's solution, 0.5 g of yeast extract, 1.0 g of proteose peptone, 5 ml of fetal bovine serum, 10 ml of horse serum, 500 μl of *Bacillus licheniformis* suspension, 300 mg of aseptic starch.

In the Example 4, formulas and preparing method of the Ringer's solution are identical to the Example 1.

In the Example 4 of the present invention, a method for preparing the medium for culturing the *Balantidium ctenopharyngodoni* in vitro, specifically comprising steps of:

(a) accurately weighing 0.5 g of yeast extract and 1.0 g of proteose peptone, to be put into a conical flask with a volume of 250 ml, adding 100 ml of Ringer's solution, adjusting pH to 7.0-7.5, sealing the conical flask with foil paper, autoclaving at 121° C. for 20 min and then storing after the medium is cooled to 4° C.;

(b) split charging each of a plurality of 25 ml sterile anaerobic bottles with a 5 ml medium formed in the step (a), and separately adding 25 μl of *Bacillus licheniformis* suspension to each of the sterile anaerobic bottles, and putting the plurality of the sterile anaerobic bottles into a microbial shaker at 30° C. for culturing until a concentration is $4 \times 10^9$ CFU/ml, wherein a rotation speed of the shaker is 150 rpm;

(c) respectively adding 250 μl of fetal bovine serum, 500 μl of horse serum and 15 mg of aseptic starch to each of the sterile anaerobic bottles containing the medium formed in the step (b), and then placing at 15° C. for use, wherein at this time, the medium for culturing the *Balantidium ctenopharyngodoni* in vitro is completed.

A method for culturing the *Balantidium ctenopharyngodoni* in vitro, comprising steps of:

(1) taking out a plurality of anaerobic bottles containing the medium for culturing the *Balantidium ctenopharyngodoni* cultured in vitro;

(2) anesthetizing the grass carp with MS-222 to be put into a dissection tray, rinsing a anus near with sterile water, dissecting the grass carp with a sterile anatomical scissors, taking out viscera, cutting the hindgut to be put into a sterile petri dish with a diameter of 9 cm; opening the hindgut with a small anatomical scissors, and scraping luminal contents of the hindgut with a sterile scalpel to be put into a sterile petri dish with a diameter of 5.5 cm; adding 5 ml of sterile saline solution with a concentration of 0.65% (w/v); standing for 3 min; examining the *Balantidium ctenopharyngodoni* inhabited in the contents of the hindgut under a stereomicroscope; after finding the *Balantidium ctenopharyngodoni*, aspirating with a sterile glass micropipette to another petri dish containing sterile saline with a concentration of 0.65% (w/v); after washing 3 times, replacing with new sterile saline, and placing in a constant temperature incubator at 15° C. for 25 min;

(3) taking out the medium in the constant temperature incubator and the petri dish containing the *Balantidium ctenopharyngodoni*, and taking 10 active *Balantidium ctenopharyngodoni* with a sterile glass micropipette to be inoculated to a anaerobic bottle containing the medium for the *Balantidium ctenopharyngodoni*, sealing the anaerobic bottle with rubber stopper after being continuously filled with nitrogen for 5 minutes, and placing in a constant temperature incubator at 15° C. for 48 hours;

(4) taking out the anaerobic bottle containing ciliates in the constant temperature incubator, pouring out the culture into a sterile petri dish, and transferring all the *Balantidium ctenopharyngodoni* to another anaerobic bottle containing 3 ml of fresh medium for culturing the *Balantidium ctenopharyngodoni* in vitro with a sterile glass micropipette under a stereomicroscope, and meanwhile recording a number of all the *Balantidium ctenopharyngodoni*, then filling the anaerobic bottle with nitrogen for 5 min and sealing, then continuing to place in constant temperature incubator at 15° C. for 48 hours;

(5) transferring all the *Balantidium ctenopharyngodoni* after the constant temperature culture in step (4) in the anaerobic bottle to another anaerobic bottle, and meanwhile recording a number of all the *Balantidium ctenopharyngodoni*, then filling the anaerobic bottle with nitrogen for 5 min and sealing, then continuing to place in constant temperature incubator at a 15° C. for 48 hours; (6) transferring all the *Balantidium ctenopharyngodoni* after the constant temperature culture in step (5) in the anaerobic bottle to another anaerobic bottle, repeating transferring and culturing once every 48 hours to make the *Balantidium ctenopharyngodoni* continuing to multiply, and preparing fresh medium for culturing the *Balantidium ctenopharyngodoni* in vitro in time during the experiment.

The nitrogen mentioned above is pure nitrogen and a purity of nitrogen is greater than 99.99%.

In the Example 4, the in vitro culture experiment of the *Balantidium ctenopharyngodoni* continued for one year, and the *Balantidium ctenopharyngodoni* were observed and counted once every 48 hours. During this one-year period, the *Balantidium ctenopharyngodoni* in the medium remains strong fertility and vitality.

In addition, the applicants respectively observed a living *Balantidium ctenopharyngodoni* and cell division of the *Balantidium ctenopharyngodoni* under a microscope after being cultured for 1 year in vitro. The result indicates that the medium prepared by the present invention enables the split-proliferation cell division and long-term stable culture of the *Balantidium ctenopharyngodoni*, and maintains vigorous vitality and fecundity during the cultivation process.

What is claimed is:

1. A medium formulated for culturing *Balantidium ctenopharyngodoni* in vitro, comprising: 100 ml of Ringer's solution, 0.5 g of yeast extract, 1.0 g of proteose peptone, 3-6 ml of fetal bovine serum, 6-10 ml of horse serum, 300-500 µl of *Bacillus licheniformis* suspension having a concentration of $2 \times 10^9$-$6 \times 10^9$ colony forming units (CFU)/ml, and 200-300 mg of aseptic starch;
wherein the medium has a pH in the range of 7.0 to 7.5.

2. The medium as recited in claim 1, wherein the Ringer's solution comprises: 6.5 g of sodium chloride (NaCl), 0.14 g of potassium chloride (KCl), 0.12 g of calcium chloride ($CaCl_2$), 0.2 g of sodium bicarbonate ($NaHCO_3$), 0.01 g of sodium dihydrogen phosphate ($NaH_2PO_4$), and 1000 ml of distilled water.

3. A method for preparing a medium formulated for culturing *Balantidium ctenopharyngodoni* in vitro, comprising steps of:
    (a) weighing 0.5 g of yeast extract and 1.0 g of proteose peptone, adding 100 ml of Ringer's solution, adjusting pH to 7.0-7.5, autoclaving and then storing at 4° C.;
    (b) split charging a plurality of sterile anaerobic bottles with the medium formed in the step (a) by a volume of 3-5 ml, and separately adding 9-25 µl of a *Bacillus licheniformis* suspension to each of the sterile anaerobic bottles, and putting the plurality of the sterile anaerobic bottles into a microbial shaker at 30° C. for culturing until the concentration of *Bacillus licheniformis* reaches $2 \times 10^9$-$6 \times 10^9$ colony forming units (CFU)/ml suspension; and
    (c) adding 90-250 µl of fetal bovine serum, 180-500 µl of horse serum and 6-15 mg of aseptic starch to each of the sterile anaerobic bottles containing the medium obtained from the step (b), and then placing the formulated medium in the anaerobic bottles at 15° C. for use.

4. The method as recited in claim 3, wherein an autoclaving temperature in the step (a) is 121° C., and an autoclaving time is 20 min.

5. The method as recited in claim 3, wherein a speed of the microbial shaker in the step (b) is 150 rpm.

6. The method as recited in claim 3, wherein the Ringer's solution is prepared by steps of:
    (i) sequentially dissolving 6.5 g of sodium chloride (NaCl), 0.14 g of potassium chloride (KCl), 0.2 g of sodium bicarbonate ($NaHCO_3$), and 0.01 g of sodium dihydrogen phosphate ($NaH_2PO_4$) in 999 ml distilled water to prepare a solution 1;
    (ii) preparing a calcium chloride ($CaCl_2$) solution having a mass concentration of 12%; and
    (iii) adding 1 ml of the $CaCl_2$ solution obtained from the step (ii) to the solution 1, mixing uniformly to obtain the Ringer's solution, and storing it at room temperature for use.

7. A method for culturing *Balantidium ctenopharyngodoni* in vitro, comprising steps of:
    (1) preparing a plurality of anaerobic bottles sterilized, wherein each of the anaerobic bottles contain 3-5 ml of the formulated medium according to claim 1;
    (2) dissecting an intestine of a grass carp infected with *Balantidium ctenopharyngodoni*, collecting the *Balantidium ctenopharyngodoni* under a stereomicroscope, placing the collected *Balantidium ctenopharyngodoni* in a sterile petri dish containing an aseptic saline solution, gently washing 2 to 3 times, replacing the aseptic saline solution, then placing the petri dish with washed *Balantidium ctenopharyngodoni* in a constant temperature incubator at 15° C. and incubating it for a period of time;
    (3) taking out free *Balantidium ctenopharyngodoni* from the petri dish obtained from the step (2) under the stereomicroscope, inoculating free *Balantidium ctenopharyngodoni* into the medium of one of the anaerobic bottles from the step (1), continuously filling nitrogen for 3-5 minutes, sealing the bottle with rubber stopper, and placing the inoculated anaerobic bottles at a constant temperature of 15° C. for culturing for 48-72 h; and
    (4) transferring all the cultured *Balantidium ctenopharyngodoni* from step (3) to a second anaerobic bottle filling the second anaerobic bottle with nitrogen for 3-5 minutes, sealing, and culturing in identical conditions recited in the step (3), and repeating transferring and culturing steps every 48-72 hours to proliferate the *Balantidium ctenopharyngodoni* continuously.

8. The method as recited in claim 7, wherein the aseptic saline solution has sodium chloride (NaCl) at a mass to volume concentration of 0.65%.

9. The method as recited in claim 7, wherein the nitrogen is is greater than 99.99% pure.

10. The method as recited in claim 7, wherein the incubation period in step (2) is in the range of 20-30 minutes.

* * * * *